United States Patent
Cho et al.

(10) Patent No.: US 10,336,842 B2
(45) Date of Patent: Jul. 2, 2019

(54) TRANSITION METAL COMPOUND AND CATALYST COMPOSITION INCLUDING THE SAME

(71) Applicant: LG CHEM, LTD., Seoul (KR)

(72) Inventors: Yoon Hee Cho, Daejeon (KR); Jin Sam Gong, Daejeon (KR); Jung Ho Jun, Daejeon (KR); Choong Hoon Lee, Daejeon (KR); Seung Hwan Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 42 days.

(21) Appl. No.: 15/538,463

(22) PCT Filed: Jul. 1, 2016

(86) PCT No.: PCT/KR2016/007144
§ 371 (c)(1),
(2) Date: Jun. 21, 2017

(87) PCT Pub. No.: WO2017/003261
PCT Pub. Date: Jan. 5, 2017

(65) Prior Publication Data
US 2017/0349684 A1     Dec. 7, 2017

(30) Foreign Application Priority Data
Jul. 2, 2015   (KR) .................. 10-2015-0094693

(51) Int. Cl.
| | |
|---|---|
| C08F 4/6592 | (2006.01) |
| C08F 210/16 | (2006.01) |
| C07F 17/00 | (2006.01) |
| C07D 333/76 | (2006.01) |
| C07F 7/00 | (2006.01) |
| C07F 7/02 | (2006.01) |
| C07F 7/28 | (2006.01) |
| C08F 10/00 | (2006.01) |
| C07F 7/10 | (2006.01) |

(52) U.S. Cl.
CPC .......... *C08F 210/16* (2013.01); *C07D 333/76* (2013.01); *C07F 7/00* (2013.01); *C07F 7/02* (2013.01); *C07F 7/10* (2013.01); *C07F 7/28* (2013.01); *C07F 17/00* (2013.01); *C08F 4/6592* (2013.01); *C08F 10/00* (2013.01)

(58) Field of Classification Search
CPC .............................. C07F 17/00; C09F 4/6592
See application file for complete search history.

(56) References Cited

U.S. PATENT DOCUMENTS

| | | | |
|---|---|---|---|
| 5,064,802 A | 11/1991 | Stevens et al. | |
| 6,399,710 B1 | 6/2002 | Finerman et al. | |
| 6,548,686 B2 | 4/2003 | Nabika et al. | |
| 7,635,781 B2 | 12/2009 | Nifant'ev et al. | |
| 2002/0147286 A1 | 10/2002 | Resconi et al. | |
| 2004/0220050 A1 | 11/2004 | Frazier et al. | |
| 2004/0236115 A1 | 11/2004 | Nifantev et al. | |
| 2006/0160967 A1 | 7/2006 | Voskoboynikov et al. | |
| 2006/0160968 A1 | 7/2006 | Voskoboynikov et al. | |
| 2006/0183874 A1 | 8/2006 | Voskoboynikov et al. | |
| 2007/0015657 A1 | 1/2007 | Rieger et al. | |
| 2007/0135623 A1 | 6/2007 | Voskoboynikov et al. | |
| 2008/0287692 A1 | 11/2008 | Nifant'ev et al. | |
| 2010/0062927 A1 | 3/2010 | Lee et al. | |
| 2010/0113717 A1 | 5/2010 | Voskoboynikov et al. | |
| 2011/0172451 A1 | 7/2011 | Lee et al. | |
| 2011/0177935 A1 | 7/2011 | Lee et al. | |
| 2011/0288249 A1 | 11/2011 | Voskoboynikov et al. | |
| 2012/0202956 A1 | 8/2012 | Voskoboynikov et al. | |

FOREIGN PATENT DOCUMENTS

| | | |
|---|---|---|
| CN | 1282348 A | 1/2001 |
| CN | 1753914 A | 3/2006 |
| JP | 2004-530689 A | 10/2004 |
| KR | 10-2001-0112350 A | 12/2001 |
| KR | 10-0976131 B1 | 8/2010 |
| KR | 10-2015-00367631 A | 4/2015 |
| WO | WO 02/092564 A2 | 11/2002 |
| WO | WO 2006/065844 A2 | 6/2006 |

OTHER PUBLICATIONS

XP 002774652, The Dow Chemical Company, Technical Information of Engage 8200, Nov. 30, 2000, Retrieved from the Internet: URL:http://dowglobal.ides.comjdocselect.aspx?l=48244&E=30962&DOC=DOWTDS&DS=123&DK=STD&DC=en.
European Search Report for Appl. No. 16818294.7 dated Nov. 8, 2017.
XP 002774650, The Dow Chemical Company, Technical information of Engage 8003, Nov. 30, 2000, Retrieved from the Internet: http://dowglobal.ides.comjdocselect.aspx?l=48244&E=30930&DOC=DOWTDS&DS=123&DK=STD&DC=en.
XP 002774651, The Dow Chemical Company, Technical Information of Engage 8100, Nov. 30, 2000, Retrieved from the Internet: URL:http://dowglobal.ides.comjdocselect.aspx?l=48244&E=30946&DOC=DOWTDS&DS=123&DK=STD&DC=en.
XP 002774653, The Dow Chemical Company, Technical Information of Engage 8440, Nov. 30, 2000, Retrieved from the Internet: URL:http://dowglobal.ides.comjdocselect.aspx?l=48244&E=30968&DOC=DOWTDS&DS=123&DK=STD&DC=en.
XP 002774654, The Dow Chemical Company, Technical Information of Engage 8452, Nov. 30, 2000, Retrieved from the Internet: URL:http://dowglobal.ides.comjdocselect.aspx?l=48244&E=30971&DOC=DOWTDS&DS=123&DK=STD&DC=en.

(Continued)

*Primary Examiner* — Caixia Lu
(74) *Attorney, Agent, or Firm* — Birch, Stewart, Kolasch & Birch, LLP

(57) ABSTRACT

The present disclosure provides a novel transition metal compound having excellent structural stability together with polymerization reactivity, and thereby is useful as a catalyst in preparing an olefin-based polymer, particularly, a high molecular weight and low density olefin-based polymer, and a catalyst composition including the same.

7 Claims, No Drawings

(56) References Cited

OTHER PUBLICATIONS

XP 055415013, The Dow Chemical Company, Technical Information of Engage 7447, May 1, 2008, Retrieved from the Internet: URL:http://msdssearch.dow.com/PublishedliteratureDOWCOM/dh0134/0901b80380134edb.pdf?filepath=elastomers/pdfs/noreg/774-00027.pdf&fromPage=GetDoc.

XP 055415019, The Dow Chemical Company, Technical Information of Engage 7467, May 1, 2008, Retrieved from the Internet: URL:http://msdssearch.dow.com/PublishedliteratureDOWCOM/dh0134/0901b80380134ee7.pdf?filepath=elastomers/pdfs/noreg/774-00028.pdf&fromPage=GetDoc.

XP 055415318, The Dow Chemical Company, Technical Information of ENR 7256.00, May 1, 2008, Retrieved from the Internet: URL:http://msdssearch.dow.com/PublishedliteratureDOWCOM/dh0134/0901b80380134e92.pdf?filepath=elastomers/pdfs/noreg/774-00022.pdf&fromPage=GetDoc.

Deisenhofer et al., "Asymmetric Metallocene Catalysts Based on Dibenzothiophene: A New Approach to High Molecular Weight Polypropylene Plastomers," Organometallics, vol. 22, No. 17, Aug. 18, 2003 (published on web Jul. 22, 2003), pp. 3495-3501.

Partial Supplementary European Search Report for European Application No. 16818294.7, dated Jul. 26, 2017.

Alexander Rau et al., "Synthesis and application in high-pressure polymerization of a titanium complex with a linked cyclopentadienyl-phenoxide ligand", Journal of Organometallic Chemistry, 2000, vol. 608, pp. 71-75.

Esther E. C. G. Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group", Organometallics, 1998, vol. 17, pp. 1652-1654.

International Search Report for PCT/KR2016/007144 (PCT/ISA/210) dated Oct. 11, 2016.

Luke E. Turner et al., "Facile resolution of constrained geometry indenyl-phenoxide ligation", Chemical Communications, 2003, pp. 1034-1035.

Steven D. R. Christie et al., "Novel Routes to Bidentate Cyclopentadienyl-Alkoxide Complexes of Titanium: Synthesis of ($\eta$5-$\sigma$-C5R14CHR2CH2CR3R4O)TiCl2", Organometallics, 1999, vol. 18, pp. 348-359.

Technical Information of ENGAGE™ 8842: Polyolefin Elastomer, Nov. 30, 2000, Retrieved from <URL:http://dowglobal.ides.com/docselect.aspx?I=48244&E=49414&DOC=DOWTDS&DS=123&DK=STD&DC=en> on Oct. 11, 2016.

Vernon C. Gibson et al., "Advances in Non-Metallocene Olefin Polymerization Catalysis", Chemical Reviews, 2003, vol. 103, pp. 283-315.

You-Xian Chen et al., "A Novel Phenolate "Constrained Geometry" Catalyst System. Efficient Synthesis, Structural Characterization, and $\alpha$-Olefin Polymerization Catalysis", Organometallics, 1997, vol. 16, pp. 5958-5963.

Yuetao Zhang et al., "Constrained Geometry Tetramethylcyclopentadienyl-phenoxytitanium Dichlorides: Template Synthesis, Structures, and Catalytic Properties for Ethylene Polymerization", Organometallics, 2004, vol. 23, pp. 540-546.

TRANSITION METAL COMPOUND AND CATALYST COMPOSITION INCLUDING THE SAME

FIELD OF THE INVENTION

This application claims priority to and the benefits of Korean Patent Application No. 10-2015-0094693 filed with the Korean Intellectual Property Office on Jul. 2, 2015, the entire contents of which are incorporated herein by reference.

The present disclosure relates to a novel transition metal compound and a catalyst composition including the same.

DESCRIPTION OF THE RELATED ART

Dow Chemical Company introduced [Me$_2$Si(Me$_4$C$_5$)NtBu]TiCl$_2$ (Constrained-Geometry Catalyst, abbreviated as CGC hereinafter) in early 1990s (U.S. Pat. No. 5,064,802), and advantages of the CGC in a copolymerization reaction of ethylene and alpha-olefin compared to metallocene catalysts that have been known in the art may be summarized into two points as follows: (1) CGC produces a high molecular weight polymer while exhibiting high activity even at high polymerization temperatures, and (2) copolymerizability of alpha-olefin having large steric hindrance such as 1-hexene and 1-octene is very improved as well. Besides, as other properties of CGC in a polymerization reaction have been gradually known, efforts to synthesize derivatives of CGC to use as a polymerization catalyst have been actively made both in academics and industries.

As one of the approaches, syntheses of metal compounds, in which other various bridges instead of a silicon bridge and nitrogen substituents are introduced, and polymerization thereof have been tried. Representative metal compounds that have been known until recently may be listed as the following Compounds (1) to (4) (Chem. Rev. 2003, 103, 283).

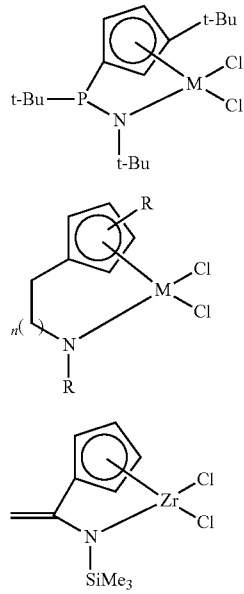

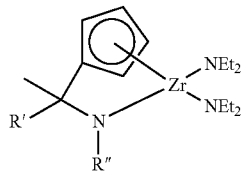

In Compounds (1) to (4), phosphorous (1), ethylene or propylene (2), methylidene (3) and methylene (4) bridges are introduced, respectively, instead of a silicon bridge of a CGC structure, however, improved results in terms of activity or copolymerization performance were not able to be obtained compared to CGC when Compounds (1) to (4) were used in ethylene polymerization or copolymerization with alpha-olefin.

In addition, as another approach, compounds having an oxido ligand instead of an amino ligand of the CGC have been actively synthesized, and polymerization using the same has also been tried in some cases. Examples thereof are summarized as follows.

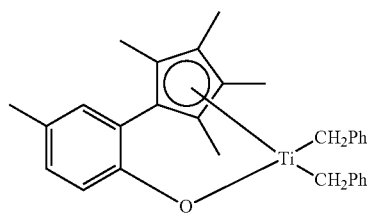

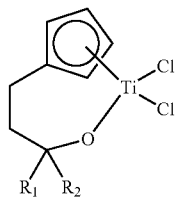

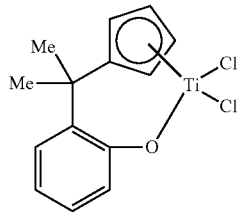

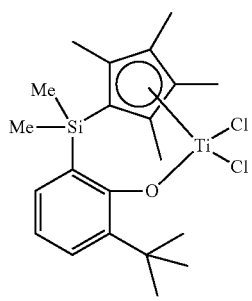

Compound (5) has been reported by T. J. Marks et al. and has a cyclopentadiene (Cp) derivative and an oxido ligand being cross-linked by an ortho-phenylene group (Organometallics 1997, 16, 5958). Compounds having the same cross-linkage and polymerization using the same have also been reported by Mu et al. (Organometallics 2004, 23, 540). In addition, an indenyl ligand and an oxido ligand being cross-linked by the same ortho-phenylene group has been reported by Rothwell et al. (Chem. Commun. 2003, 1034). Compound (6) has been reported by Whitby et al., and has a cyclopentanienyl ligand and an oxido ligand being bridged by 3 carbons (Organometallics 1999, 18, 348), and such catalysts have been reported to exhibit activity for syndiotactic polystyrene polymerization. Similar compounds have also been reported by Hessen et al. (Organometallics 1998, 17, 1652). Compound (7) has been reported by Rau et al., and exhibits activity for ethylene polymerization and ethylene/1-hexene copolymerization at a high temperature and a high pressure (210° C., 150 mPa) (J. Organomet. Chem. 2000, 608, 71). After that, Sumitomo Corporation applied for a patent on the synthesis of catalysts having similar structures thereto (8) and high temperature and high pressure polymerization using the same (U.S. Pat. No. 6,548,686). However, among the above-mentioned attempts, only a small number of catalysts are actually used in commercial factories. Accordingly, catalysts exhibiting enhanced polymerization efficiency, and simple methods for preparing such catalysts have been required.

DISCLOSURE OF THE INVENTION

Technical Problem

The present disclosure is directed to providing a novel transition metal compound having excellent polymerization reactivity and structural stability, and thereby useful in preparing an olefin-based polymer, particularly, a low density olefin-based polymer.

The present disclosure is also directed to providing a catalyst composition including the transition metal compound, and thereby useful in preparing an olefin-based polymer, particularly, a low density olefin-based polymer.

The present disclosure is also directed to providing an olefin-based polymer prepared using the catalyst composition including the transition metal compound.

The present disclosure is also directed to providing a ligand compound useful in preparing the transition metal compound.

Technical Solution

The present disclosure has been made in view of the above, and one embodiment of the present disclosure provides a transition metal compound of the following Chemical Formula 1:

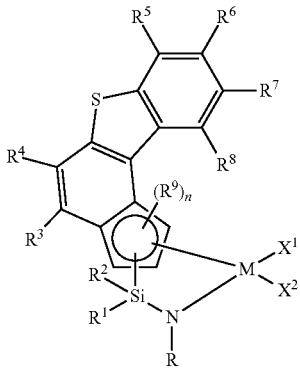

[Chemical Formula 1]

In Chemical Formula 1,

M is a group 4 transition metal,

R is selected from the group consisting of an alkyl group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and combinations thereof, $R^1$ and $R^2$ are each independently selected from the group consisting of a hydrogen atom, an alkyl group having 1 to 20 carbon atoms, an alkenyl group having 2 to 20 carbon atoms, a haloalkyl group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and combinations thereof, or $R^1$ and $R^2$ are linked to each other to form an aliphatic ring having 3 to 20 carbon atoms or an aromatic ring having 6 to 20 carbon atoms, $R^3$ to $R^8$ are each independently selected from the group consisting of a hydrogen atom, a halogen group, an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, an alkoxy group having 1 to 20 carbon atoms, an aryloxy group having 6 to 20 carbon atoms, a silyl group and combinations thereof, or adjacent two or more functional groups among $R^3$ to $R^8$ are linked to each other to form an aliphatic ring having 3 to 20 carbon atoms or an aromatic ring having 6 to 20 carbon atoms, $R^9$ is selected from the group consisting of an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, a silyl group, and a metalloid radical of a group 14 metal substituted with a hydrocarbyl group having 1 to 20 carbon atoms, $X^1$ and $X^2$ are each independently selected from the group consisting of a halogen group, an alkyl group having 1 to 20 carbon atoms, an alkenyl group having 2 to 20 carbon atoms, an aryl group having 6 to 20 carbon atoms, an alkylaryl group having 7 to 20 carbon atoms, an arylalkyl group having 7 to 20 carbon atoms, an alkylamino group having 1 to 20 carbon atoms, an arylamino group having 6 to 20 carbon atoms and an alkylidene group having 1 to 20 carbon atoms, R, $R^1$ to $R^9$, $X^1$ and $X^2$ are each independently unsubstituted or substituted with one or more substituents selected from the group consisting of a halogen group, an alkyl group having 1 to 20 carbon atoms, a haloalkyl group having 1 to 20 carbon atoms, an alkenyl group having 2 to 20 carbon atoms, an alkoxy group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and an aryloxy group having 6 to 20 carbon atoms, and n is an integer of 1 or 2, and when n is an integer of 2, two $R^9$s are the same as or different from each other.

Another embodiment of the present disclosure provides a catalyst composition including the transition metal compound of Chemical Formula 1.

Still another embodiment of the present disclosure provides an olefin-based polymer prepared using the catalyst composition, having density of 0.9 g/cc or less, and having a melt index of 1 g/min to 20 g/min under a load of 2.16 kg.

Yet another embodiment of the present disclosure provides a ligand compound of the following Chemical Formula 2 useful in preparing the transition metal compound of Chemical Formula 1.

[Chemical Formula 2]

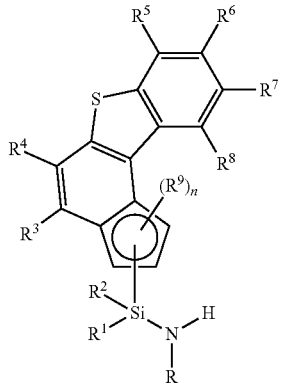

In Chemical Formula 2, R, $R^1$ to $R^9$, and n have the same definitions as above.

Advantageous Effects

In a transition metal compound according to the present disclosure, a group 4 transition metal as a central metal is linked by a dibenzothiophene-fused cyclopentadienyl group having electrons sufficiently and widely delocalized while having a rigid planar structure, and an amino group substituted with a silyl group, and therefore, the transition metal compound is capable of exhibiting excellent structural stability together with excellent polymerization reactivity by maintaining a pentagonal ring structure. As a result, the transition metal compound is useful for olefin-based polymers, particularly, high molecular weight and low density polyethylene, and is useful in preparing a copolymer of ethylene and alpha-olefin since approaches of monomers having large steric hindrance are more facilitated structurally.

MODE FOR CARRYING OUT THE INVENTION

Hereinafter, the present disclosure will be described in more detail in order to illuminate the present disclosure.

Terms or words used in the present specification and the claims are not to be interpreted limitedly to common or dictionary meanings, and shall be interpreted as meanings and concepts corresponding to technological ideas of the present disclosure based on a principle in which inventors may suitably define the concepts of terms in order to describe their own invention in the best possible way.

In the present specification, unless particularly defined otherwise, an alkyl group means a linear or branched aliphatic saturated hydrocarbon group having 1 to 20 carbon atoms. Specifically, the alkyl group includes a linear or branched alkyl group having 1 to 20 carbon atoms and more specifically 1 to 6 carbon atoms. Specific examples of the alkyl group may include a methyl group, an ethyl group, an n-propyl group, an isopropyl group, an n-butyl group, an isobutyl group, a sec-butyl group, a t-butyl group, a pentyl group, an iso-amyl group, a hexyl group or the like.

In the present specification, unless particularly defined otherwise, an alkoxy group means a linear or branched alkyl group having 1 to 20 carbon atoms bonding with oxygen (—$OR_a$). Specifically, the alkyl group ($R_a$) includes an alkyl group having 1 to 20 carbon atoms and more specifically 1 to 6 carbon atoms. Specific examples of the alkoxy group may include a methoxy group, an ethoxy group, a propoxy group, a butoxy group, a t-butoxy group or the like.

In the present specification, unless particularly defined otherwise, an alkenyl group means a linear or branched aliphatic unsaturated hydrocarbon group having 2 to 20 carbon atoms including a carbon-carbon double bond. Specifically, the alkenyl group includes an alkenyl group having 2 to 6 carbon atoms. Specific examples of the alkenyl group may include an ethenyl group, a propenyl group, a butenyl group or the like.

In the present specification, unless particularly defined otherwise, a cycloalkyl group means a cyclic saturated hydrocarbon group having 3 to 20 carbon atoms. Specifically, the cycloalkyl group includes a cycloalkyl group having 3 to 6 carbon atoms. Specific examples of the cycloalkyl group may include a cyclopropyl group, a cyclobutyl group, a cyclohexyl group or the like.

In the present specification, unless particularly defined otherwise, an aryl group means a carbocycle aromatic radical having 6 to 20 carbon atoms including one or more rings, and the rings may be attached together using a pendant method or fused. Specifically, the aryl group includes an aryl group having 6 to 20 carbon atoms and more specifically 6 to 12 carbon atoms. Specific examples of the aryl group may include a phenyl group, a naphthyl group, a biphenyl group or the like.

In the present specification, unless particularly defined otherwise, an arylalkyl group means a functional group (Ar—$R_a$—) substituting a linear or branched alkyl group ($R_a$) with an aryl group (Ar), an aromatic hydrocarbon group. Specifically, the arylalkyl group includes an arylalkyl group having 7 to 20 carbon atoms and more specifically 7 to 12 carbon atoms. Specific examples of the arylalkyl group may include a benzyl group, a phenethyl group or the like.

In the present specification, unless particularly defined otherwise, an alkylaryl group means a functional group ($R_a$—Ar—) substituting an aromatic hydrocarbon group (Ar) with a linear or branched alkyl group ($R_a$). Specifically, the alkylaryl group includes an alkylaryl group having 7 to 20 carbon atoms and more specifically 7 to 12 carbon atoms.

In the present specification, unless particularly defined otherwise, an aryloxy group means an aryl group bonding with oxygen (—OAr), and herein, the aryl group has the same definition as above. Specifically, the aryloxy group includes an aryloxy group having 6 to 20 carbon atoms and more specifically 6 to 12 carbon atoms. Specific examples of the aryloxy group may include phenoxy or the like.

In the present specification, unless particularly defined otherwise, a silyl group means a —$SiH_3$ radical derived from silane, and at least one of hydrogen atoms in the silyl group may be substituted with various organic groups such as an alkyl group ($R_a$) or a halogen group.

In the present specification, unless particularly defined otherwise, an alkylamino group means a functional group substituting at least one of hydrogens in the amino group (—$NH_2$) with an alkyl group ($R_a$), and herein, the alkyl group ($R_a$) has the same definition as above. Specifically, the alkylamino group may be —$N(R_b)_2$ (herein, $R_b$s may each be a hydrogen atom or a linear or branched alkyl group having 1 to 20 carbon atoms, however, both $R_b$s are not hydrogen atoms at the same time).

In the present specification, unless particularly defined otherwise, an arylamino group means a functional group substituting at least one of hydrogens in the amino group (—NH₂) with an aryl group (Ar), and herein, the aryl group has the same definition as above.

In the present specification, unless particularly defined otherwise, an alkylidene group means a divalent aliphatic hydrocarbon group removing two hydrogen atoms from the same carbon of the alkyl group. Specifically, the alkylidene group includes an alkylidene group having 1 to 20 carbon atoms and more specifically 1 to 12 carbon atoms. Specific examples of the alkylidene group may include a propan-2-ylidene group or the like.

In the present specification, unless particularly defined otherwise, a hydrocarbyl group means a monovalent hydrocarbon group having 1 to 60 carbon atoms formed only with carbon and hydrogen regardless of its structure such as an alkyl group, an aryl group, an alkenyl group, an alkylaryl group and an arylalkyl group.

In the present specification, unless particularly defined otherwise, a metalloid radical is a metalloid radical of a group 14 (group 4A) metal substituted with a hydrocarbyl group having 1 to 20 carbon atoms. The metalloid radical is electronically unsaturated, and may perform a role of Lewis acid. The group 14 metal may include silicon (Si), germanium, tin, arsenic or the like. Specifically, the metalloid radical may include a silyl group such as a trimethylsilyl group, a triethylsilyl group, an ethyldimethylsilyl group and a methyldiethylsilyl group; a triphenylgermyl group, a trimethylgermyl group or the like.

In the present specification, unless particularly defined otherwise, 'combinations thereof' means two or more functional groups bonding through a linking group such as a single bond, a double bond (ethylene group), a triple bond (acetylene group) or a alkylene group having 1 to 20 carbon atoms (for example, a methylene group (—CH₂—), an ethylene group (—CH₂CH₂—) or the like), or two or more functional groups being fused and linked.

A transition metal compound according to one embodiment of the present disclosure has a structure of the following Chemical Formula 1:

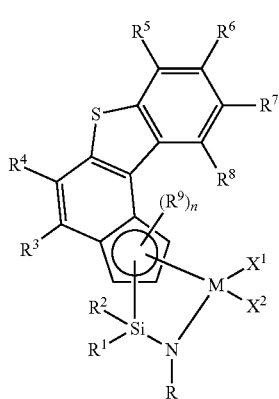

[Chemical Formula 1]

In Chemical Formula 1,

M is a group 4 transition metal,

R is selected from the group consisting of an alkyl group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and combinations thereof, $R^1$ and $R^2$ are each independently selected from the group consisting of a hydrogen atom, an alkyl group having 1 to 20 carbon atoms, an alkenyl group having 2 to 20 carbon atoms, a haloalkyl group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and combinations thereof, or $R^1$ and $R^2$ are linked to each other to form an aliphatic ring having 3 to 20 carbon atoms or an aromatic ring having 6 to 20 carbon atoms, $R^3$ to $R^8$ are each independently selected from the group consisting of a hydrogen atom, a halogen group, an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, an alkoxy group having 1 to 20 carbon atoms, an aryloxy group having 6 to 20 carbon atoms, a silyl group and combinations thereof, or adjacent two or more functional groups among $R^3$ to $R^8$ are linked to each other to form an aliphatic ring having 3 to 20 carbon atoms or an aromatic ring having 6 to 20 carbon atoms, $R^9$ is selected from the group consisting of an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, a silyl group, and a metalloid radical of a group 14 metal substituted with a hydrocarbyl group having 1 to 20 carbon atoms, $X^1$ and $X^2$ are each independently selected from the group consisting of a halogen group, an alkyl group having 1 to 20 carbon atoms, an alkenyl group having 2 to 20 carbon atoms, an aryl group having 6 to 20 carbon atoms, an alkylaryl group having 7 to 20 carbon atoms, an arylalkyl group having 7 to 20 carbon atoms, an alkylamino group having 1 to 20 carbon atoms, an arylamino group having 6 to 20 carbon atoms and an alkylidene group having 1 to 20 carbon atoms, n is an integer of 1 or 2, and when n is an integer of 2, two $R^9$s are the same as or different from each other.

In addition, each functional group in Chemical Formula 1, R, $R^1$ to $R^9$, $X^1$ and $X^2$ may be each independently further substituted with one or more substituents selected from the group consisting of a halogen group, an alkyl group having 1 to 20 carbon atoms, a haloalkyl group having 1 to 20 carbon atoms, an alkenyl group having 2 to 20 carbon atoms, an alkoxy group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms and an aryloxy group having 6 to 20 carbon atoms.

In the transition metal compound of Chemical Formula 1 according to one embodiment of the present disclosure, the metal site is linked by a dibenzothiophene-fused cyclopentadienyl (hereinafter, simply referred to as 'fused Cp') ligand introducing an amino group substituted with a silyl group, and structurally, the angle of the fused Cp-metal (M)-nitrogen (N) may be narrow, and the $X^1$-M-$X^2$ angle to which monomers for a polymer approach may be maintained as being wide. As a result, approaches of monomers having large steric hindrance may be more readily achieved. In addition, in the transition metal compound of Chemical Formula 1, the fused Cp, Si of the silyl group and nitrogen (N) of the amino group may form a more stable and rigid pentagonal ring structure with the central metal (M) due to a ring-type bonding. In other words, the nitrogen atom of the amino group is linked by two bonds with the silyl group bridge in a ring form, and therefore, a more rigid complex compound structure may be obtained. Accordingly, when used in olefin polymerization, large quantities of alpha-olefin as well as high molecular weight and low density polyolefin, particularly, linear low density polyethylene may be introduced, and as a result, very low density polyolefin copolymer having density of 0.9 g/cc or less and more specifically 0.885 g/cc or less may be prepared.

In addition, various substituents may be introduced to the fused Cp ring and the silyl group. As a result, electronic and steric environments around the metal may be controlled, and structures, physical properties and the like of the produced polyolefin may be readily controlled. Accordingly, the transition metal compound of Chemical Formula 1 may be useful as a catalyst for preparing an olefin-based polymer, however, the use is not limited thereto, and the transition metal compound is capable of being used in all usable fields.

More specifically, in Chemical Formula 1, M may be selected from the group consisting of titanium (Ti), zirconium (Zr) and hafnium (Hf), and more specifically, may be titanium (Ti).

In addition, in Chemical Formula 1, R may be more specifically selected from the group consisting of a linear or branched alkyl group having 1 to 12 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms and combinations thereof, and these functional groups may be independently unsubstituted or substituted with one or more substituents selected from the group consisting of a halogen group, an alkyl group having 1 to 10 carbon atoms, a haloalkyl group having 1 to 10 carbon atoms, an alkenyl group having 2 to 10 carbon atoms, an alkoxy group having 1 to 10 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms and an aryloxy group having 6 to 12 carbon atoms. More specifically, R may be a linear or branched alkyl group having 1 to 8 carbon atoms or an aryl group having 6 to 12 carbon atoms, and these functional groups may be unsubstituted or substituted with one or more substituents selected from the group consisting of a halogen group, an alkyl group having 1 to 10 carbon atoms and a haloalkyl group having 1 to 10 carbon atoms.

In addition, in Chemical Formula 1, $R^1$ and $R^2$ may be each independently selected from the group consisting of a hydrogen atom, a linear or branched alkyl group having 1 to 12 carbon atoms, an alkenyl group having 2 to 12 carbon atoms, a haloalkyl group having 1 to 12 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms and combinations thereof, or $R^1$ and $R^2$ may be linked to each other to form an aliphatic ring having 4 to 8 carbon atoms or an aromatic ring having 4 to 8 carbon atoms, and more specifically, $R^1$ and $R^2$ may be each independently selected from the group consisting of an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms and an alkylaryl group having 7 to 12 carbon atoms, or $R^1$ and $R^2$ may be linked to each other to form an aliphatic ring having 4 to 6 carbon atoms or an aromatic ring having 6 to 8 carbon atoms.

In addition, in Chemical Formula 1, $R^3$ to $R^8$ may be each independently selected from the group consisting of a hydrogen atom, a halogen group, an alkyl group having 1 to 12 carbon atoms, an alkenyl group having 2 to 12 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms, an alkoxy group having 1 to 12 carbon atoms, an aryloxy group having 6 to 12 carbon atoms, a silyl group and combinations thereof, or adjacent two or more functional groups among $R^3$ to $R^8$ may be linked to each other to form an aliphatic ring having 4 to 8 carbon atoms or an aromatic ring having 6 to 8 carbon atoms. More specifically, $R^3$ to $R^8$ may be each independently selected from the group consisting of a hydrogen atom, an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms and an alkylaryl group having 7 to 12 carbon atoms, or adjacent two or more functional groups among $R^3$ to $R^8$ may be linked to each other to form an aliphatic ring having 4 to 6 carbon atoms or an aromatic ring having 6 to 8 carbon atoms.

In addition, in Chemical Formula 1, $R^9$ is selected from the group consisting of an alkyl group having 1 to 12 carbon atoms, an alkenyl group having 2 to 12 carbon atoms, a cycloalkyl group having 3 to 12 carbon atoms, an aryl group having 6 to 12 carbon atoms, an arylalkyl group having 7 to 12 carbon atoms, an alkylaryl group having 7 to 12 carbon atoms, a silyl group, and a metalloid radical of a group 14 metal substituted with a hydrocarbyl group having 1 to 12 carbon atoms, and more specifically, $R^9$ may be a hydrogen atom or an alkyl group having 1 to 6 carbon atoms.

In addition, in Chemical Formula 1, $X^1$ and $X^2$ may be each independently selected from the group consisting of a halogen group, an alkyl group having 1 to 6 carbon atoms, an alkenyl group having 2 to 6 carbon atoms, an aryl group having 6 to 12 carbon atoms, an alkylaryl group having 7 to 12 carbon atoms, an arylalkyl group having 7 to 12 carbon atoms, an alkylamino group having 1 to 6 carbon atoms, an arylamino group having 6 to 12 carbon atoms and an alkylidene group having 1 to 12 carbon atoms. More specifically, $X^1$ and $X^2$ may be each independently an alkyl group having 1 to 6 carbon atoms, and even more specifically a methyl group or an ethyl group.

As compounds favored for controlling electronic and steric environments around the metal (M) in Chemical Formula 1, a compound represented by the following Chemical Formula 1a or 1b may be more specifically included:

[Chemical Formula 1a]

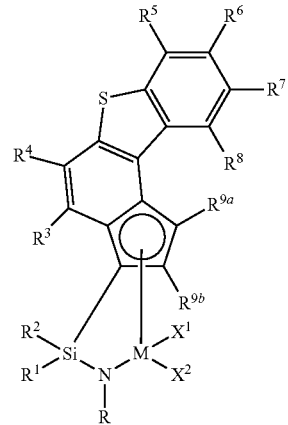

-continued

[Chemical Formula 1b]

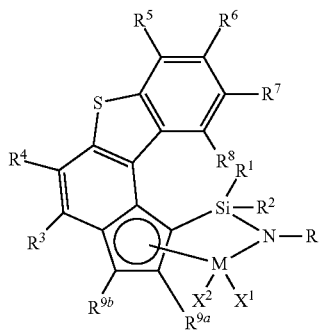

In Chemical Formula 1a or 1b, M, $R^1$ to $R^8$, R, $X^1$ and $X^2$ have the same definitions as above, $R^{9a}$ and $R^{9b}$ may be each independently selected from the group consisting of a hydrogen atom, an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, a silyl group, and a metalloid radical of a group 14 metal substituted with a hydrocarbyl group having 1 to 20 carbon atoms, or $R^{9a}$ and $R^{9b}$ may be linked to each other to form an aliphatic ring having 3 to 20 carbon atoms or an aromatic ring having 6 to 20 carbon atoms, and more specifically, $R^{9a}$ and $R^{9b}$ may be each independently selected from the group consisting of a hydrogen atom, an alkyl group having 1 to 8 carbon atoms, a cycloalkyl group having 3 to 12 carbon atoms, an aryl group having 6 to 12 carbon atoms, an arylalkyl group having 7 to 12 carbon atoms and an alkylaryl group having 7 to 12 carbon atoms, or $R^{9a}$ and $R^{9b}$ may be linked to each other to form an aliphatic ring having 4 to 6 carbon atoms or an aromatic ring having 6 to 8 carbon atoms.

More specifically, in Chemical Formulae 1a and 1b, M may be selected from the group consisting of titanium (Ti), zirconium (Zr) and hafnium (Hf), and more specifically, may be titanium (Ti), R is a linear or branched alkyl group having 1 to 8 carbon atoms or an aryl group having 6 to 12 carbon atoms, and R may be unsubstituted or substituted with one or more substituents selected from the group consisting of a halogen group, an alkyl group having 1 to 10 carbon atoms and a haloalkyl group having 1 to 10 carbon atoms, $R^1$ and $R^2$ may be each independently selected from the group consisting of an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms and an alkylaryl group having 7 to 12 carbon atoms, or $R^1$ and $R^2$ may be linked to each other to form an aliphatic ring having 4 to 6 carbon atoms or an aromatic ring having 6 to 8 carbon atoms, $R^3$ to $R^8$ may be each independently selected from the group consisting of a hydrogen atom, an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms and an alkylaryl group having 7 to 12 carbon atoms, or adjacent two or more functional groups among $R^3$ to $R^8$ may be linked to each other to form an aliphatic ring having 4 to 6 carbon atoms or an aromatic ring having 6 to 8 carbon atoms, and more specifically, $R^3$ to $R^8$ are each independently a hydrogen atom or an alkyl group having 1 to 6 carbon atoms, and $R^{9a}$ and $R^{9b}$ may be each independently selected from the group consisting of a hydrogen atom, an alkyl group having 1 to 8 carbon atoms, a cycloalkyl group having 3 to 12 carbon atoms, an aryl group having 6 to 12 carbon atoms, an arylalkyl group having 7 to 12 carbon atoms and an alkylaryl group having 7 to 12 carbon atoms, or $R^{9a}$ and $R^{9b}$ may be linked to each other to form an aliphatic ring having 4 to 6 carbon atoms or an aromatic ring having 6 to 8 carbon atoms.

Even more specifically, the transition metal compound of Chemical Formula 1 may be selected from the group consisting of compounds of the following Chemical Formulae 1-1 to 1-4:

(1-1)

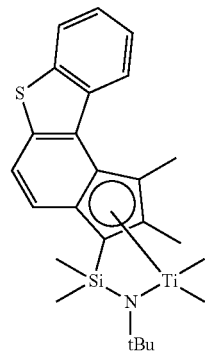

(1-2)

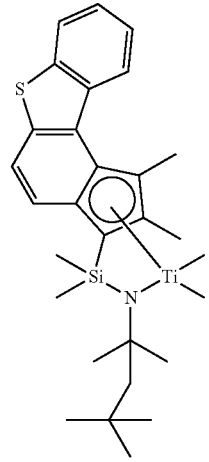

(1-3)

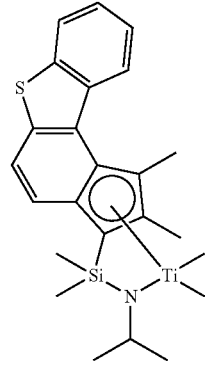

(1-4)

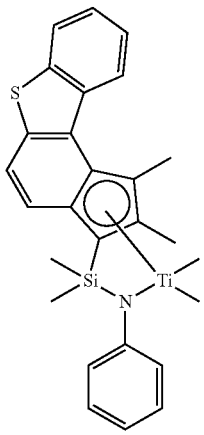

Meanwhile, the transition metal compound of Chemical Formula 1 having structures as above may be prepared using a preparation method including reacting a ligand compound of the following Chemical Formula 2 with an organolithium-based compound, and then reacting with a compound of the following Chemical Formula 3, and a Grignard reagent or an organolithium-based compound. Accordingly, another embodiment of the present disclosure provides a method for preparing the transition metal compound of Chemical Formula 1.

[Chemical Formula 2]

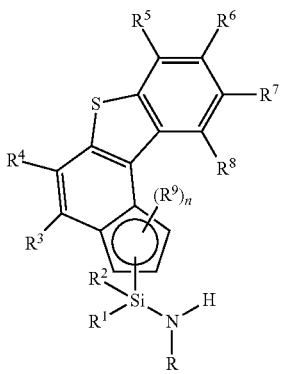

[Chemical Formula 3]

MCl$_4$ (In Chemical Formulae 2 and 3, M, R, R$^1$ to R$^9$, and n have the same definitions as above.)

In preparing the transition metal compound of Chemical Formula 1 according to the present disclosure, the ligand compound of Chemical Formula 2 may be prepared using a preparation method including reacting a compound of the following Chemical Formula 4 with a metal hydride or an organolithium compound (S1); reacting the resultantly obtained reactant with an organolithium compound and then with a silane-based compound (S2); and reacting the resultantly obtained reactant with an amine-based compound (S3).

[Chemical Formula 4]

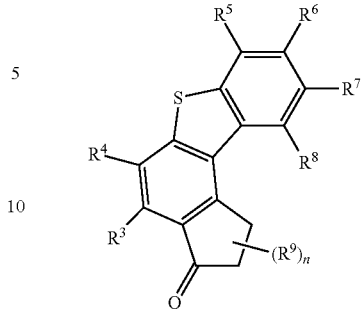

(In Chemical Formula 4, R$^3$ to R$^9$, and n have the same definitions as above)

Hereinafter, each step will be described in detail. First, Step 1 (S1) for preparing the ligand compound of Chemical Formula 2 is a step of reacting the compound of Chemical Formula 4 with a metal hydride or an organolithium compound.

The compound of Chemical Formula 4 may be prepared by mixing dibenzothiophene with a metal halide such as AlCl$_3$; and an acid halide such as tigloyl chloride, benzoyl chloride, hexanoyl chloride and butyryl chloride in a non-polar solvent such as methylene chloride, and then reacting the result at −90° C. to 25° C. Herein, for the reactant obtained as a result of the reaction, an extraction process using methylene chloride, K$_2$CO$_3$ and the like may be further carried out.

Meanwhile, in preparing the ligand compound of Chemical Formula 2, examples of the metal hydride capable of reacting with the compound of Chemical Formula 4 may include LiBH$_4$, NaBH$_4$, Mg(BH$_4$)$_2$, Ca(BH$_4$)$_2$, LiAlH$_4$, NaAlH$_4$, Ca(AlH$_4$)$_2$ or the like, and any one, or a mixture of two or more thereof may be used. The metal hydride may be used in 1 equivalent to 2 equivalents with respect to 1 equivalent of the compound of Chemical Formula 4.

On the other hand, in preparing the ligand compound of Chemical Formula 2, the organolithium-based compound capable of reacting with the compound of Chemical Formula 4 may specifically be an alkyl lithium (R$_a$—Li, the alkyl group has the same definition as above, and specifically, is a linear alkyl group having 1 to 8 carbon atoms), a cycloalkyl lithium (herein, the cycloalkyl group has the same definition as above, and specifically, is a cycloalkyl group having 3 to 12 carbon atoms), an allyl lithium, a vinyl lithium, an aryl lithium (the aryl group has the same definition as above, and specifically, is an aryl group having 6 to 12 carbon atoms), an arylalkyl lithium (the arylalkyl group has the same definition as above, and specifically, is an arylalkyl group having 7 to 12 carbon atoms) or an alkylaryl lithium (the alkylaryl group has the same definition as above, and specifically, is an arylalkyl group having 7 to 12 carbon atoms). More specifically, examples of the organolithium-based compound may include methyl lithium, ethyl lithium, isopropyl lithium, n-butyl lithium, sec-butyl lithium, t-butyl lithium, isobutyl lithium, pentyl lithium, isopentyl lithium, cyclopentyl lithium, cyclohexyl lithium, hexyl lithium, octyl lithium, allyl lithium, vinyl lithium, phenyl lithium, benzyl lithium or the like, and any one, or a mixture of two or more thereof may be used. When considering excellent reactivity with the compound of Chemical Formula 4, the organolithium-based compound may be methyl lithium, n-butyl lithium, t-butyl lithium or a mixture thereof.

The reaction between the compound of Chemical Formula 4 and the metal hydride or the organolithium compound may be carried out in an organic solvent such as methanol or tetrahydrofuran (THF).

Next, Step 2 (S2) for preparing the ligand compound of Chemical Formula 2 is a step of reacting the reactant, which is obtained as a result of reacting the compound of Chemical Formula 4 with the metal hydride or the organolithium compound, with a silane-based compound.

The silane-based compound may specifically be a dihalosilane-based compound of the following Chemical Formula 5.

[Chemical Formula 5]

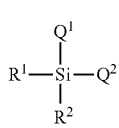

(In Chemical Formula 5, $Q^1$ and $Q^2$ are each independently a halogen group, and $R^1$ and $R^2$ have the same definitions as above.)

More specifically, the silane-based compound may be dichlorodimethylsilane or the like.

The reaction with the silane-based compound may be carried out in an organic solvent such as tetrahydrofuran.

Next, Step 3 (S3) for preparing the ligand compound of Chemical Formula 2 is a step of reacting the reactant obtained as a result of the above-mentioned reaction with an amine-based compound.

The amine-based compound may specifically be a compound of the following Chemical Formula 6.

R—NH$_2$   [Chemical Formula 6]

(In Chemical Formula 6, R has the same definition as above)

More specifically, the amine-based compound may be tert-butylamine or the like.

In addition, the reaction with the amine-based compound may be carried out at a temperature of −80° C. to 50° C.

Through the reactions as above, the ligand compound of Chemical Formula 2 useful in preparing the transition metal compound according to one embodiment of the present disclosure may be prepared.

Even more specifically, the ligand compound of Chemical Formula 2 used in preparing the transition metal compound of Chemical Formula 1 according to the present disclosure may be prepared using a method such as the following Reaction Formula 1 or 2. However, the following Reaction Formulae 1 and 2 are for illustrative purposes only, and the present disclosure is not limited thereto.

[Reaction Formula 1]

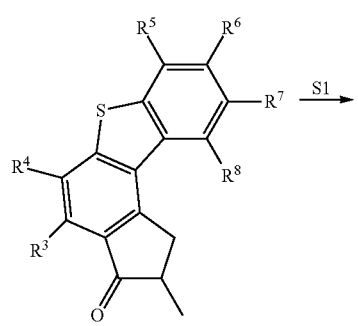

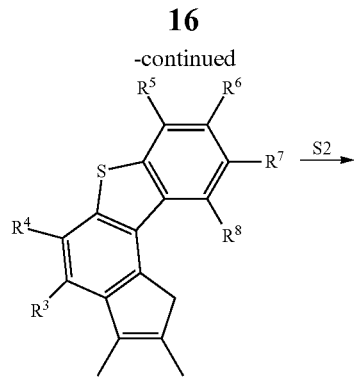

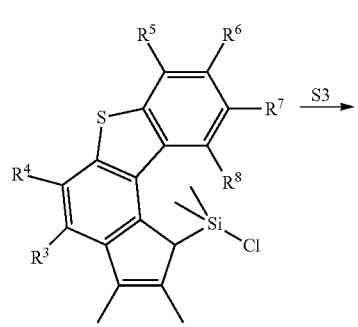

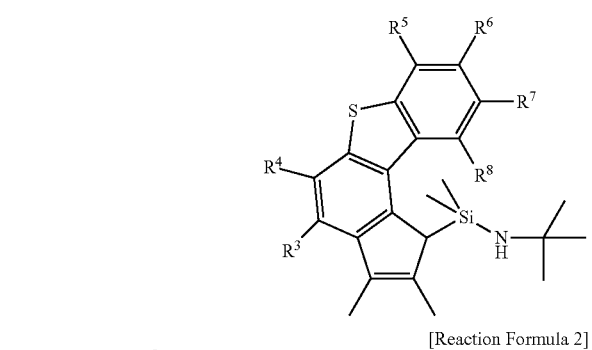

[Reaction Formula 2]

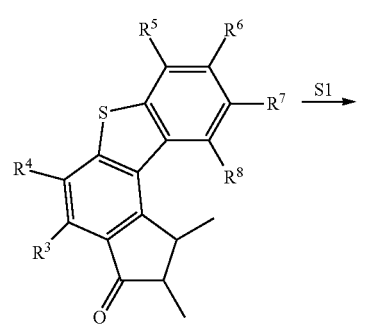

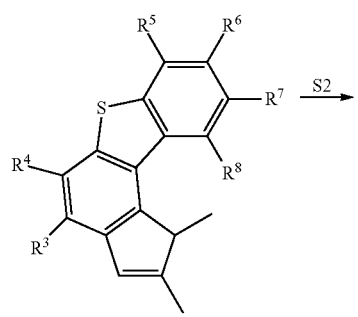

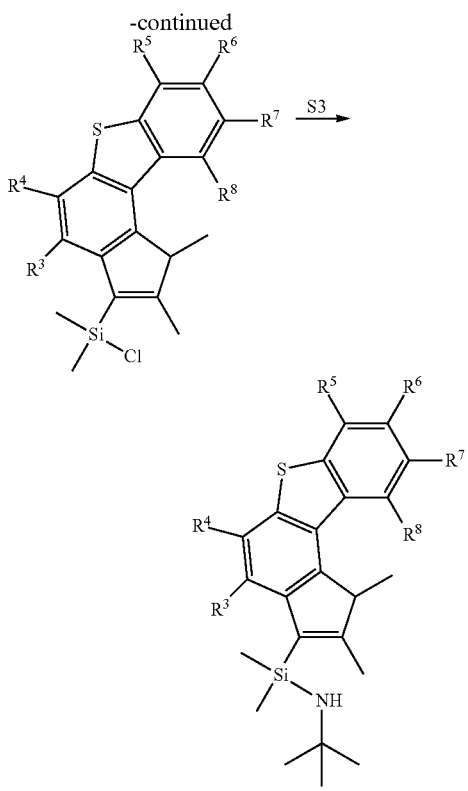

In Reaction Formulae 1 and 2, $R^3$ to $R^8$ have the same definitions as above.

Meanwhile, as the organolithium-based compound in preparing the transition metal compound of Chemical Formula 1 according to the present disclosure, the same compounds as described above may be used. The organolithium-based compound may be used in a stoichiometric ratio with respect to the ligand compound of Chemical Formula 2, and specifically, the ligand compound of Chemical Formula 2 and the organolithium-based compound may be used in a molar ratio of 1:1 to 3 and more specifically in a molar ratio of 1:1 to 2.

In addition, in preparing the transition metal compound of Chemical Formula 1 according to the present disclosure, the reaction of the ligand compound of Chemical Formula 2 and the organolithium-based compound may be carried out at a temperature of −90° C. to 10° C. and more specifically at a temperature of −78° C. to 10° C., and through the reaction of the ligand compound of Chemical Formula 2 and the organolithium-based compound, a dilithium compound is produced.

Next, in preparing the transition metal compound of Chemical Formula 1 according to the present disclosure, the compound of Chemical Formula 3, and a Grignard reagent or an organolithium-based compound are added to the reactant obtained as a result of the reaction of the ligand compound of Chemical Formula 2 and an organolithium-based compound, and reacted. Herein, the organolithium-based compound may be the same as described above.

Specifically, the compound of Chemical Formula 3 may be $TiCl_4$, $ZrCl_4$ or $HfCl_4$, and any one, or a mixture of two or more thereof may be used. In addition, the compound of Chemical Formula 3 may be used in 1 equivalent to 1.2 equivalents with respect to 1 equivalent of the ligand compound of Chemical Formula 2.

In addition, the Grignard reagent may specifically be a compound of the following Chemical Formula 7.

R'MgX        [Chemical Formula 7]

(In Chemical Formula 7, R' is selected from the group consisting of an alkyl group having 1 to 30 carbon atoms, an aryl group having 6 to 30 carbon atoms and an arylalkyl group having 7 to 30 carbon atoms, and X is a halogen group.)

More specifically, the Grignard reagent may be MeMgBr, EtMgCl (herein, Me is a methyl group and Et is an ethyl group) and the like, and may be used in 2 equivalents to 2.5 equivalents with respect to 1 equivalent of the ligand compound of Chemical Formula 2.

The reaction of the compound of Chemical Formula 3, and a Grignard reagent or an organolithium-based compound for the reactant obtained as a result of the reaction between the compound of Chemical Formula 2 and the an organolithium-based compound may be carried out at a temperature of −90° C. to 10° C. and more specifically at a temperature of −78° C. to 10° C.

From the preparation processes as above, the transition metal compound of Chemical Formula 1 having a unique structure as described above and thereby having excellent polymerization reactivity and structural stability may be prepared.

Another embodiment of the present disclosure provides a catalyst composition including the transition metal compound.

Specifically, the catalyst composition includes the transition metal compound of Chemical Formula 1, and selectively, may further include a co-catalyst preferably functioning as a counter ion, that is, an anion having weak bonding strength while cationizing the central metal by extracting $X_1$ and $X_2$ ligands in the transition metal complex so that the transition metal compound of Chemical Formula 1 becomes an active catalyst component used in preparing an ethylene homopolymer or a copolymer of ethylene and α-olefin.

The co-catalyst may be used without particular limit as long as it is known in the art such as alkyl aluminoxane, alkyl aluminum or Lewis acid. Specifically, the co-catalyst may include any one or a mixture of two or more selected from the group consisting of compounds of the following Chemical Formulae 8 to 11:

—[Al($R^{31}$)—O]$_a$—        [Chemical Formula 8]

A($R^{32}$)$_3$        [Chemical Formula 9]

[L-H]$^+$[W(D)$_4$]$^-$        [Chemical Formula 10]

[L]$^+$[W(D)$_4$]$^-$        [Chemical Formula 11]

In Chemical Formulae 8 to 11, $R^{31}$ and $R^{32}$ are each independently selected from the group consisting of a halogen group, a hydrocarbyl group having 1 to 20 carbon atoms, and a hydrocarbyl group having 1 to 20 carbon atoms substituted with a halogen group, A is aluminum or boron, Ds are each independently an aryl group having 6 to 20 carbon atoms or an alkyl group having 1 to 20 carbon atoms in which one or more hydrogen atoms may be substituted with a substituent, and herein, the substituent is at least any one selected from the group consisting of a halogen group, a hydrocarbyl group having 1 to 20 carbon atoms, an alkoxy group having 1 to 20 carbon atoms and an aryloxy group having 6 to 20 carbon atoms, H is a hydrogen atom, L is a neutral or cationic Lewis acid, W is a group 13 element, and a is an integer of 2 or greater.

In the co-catalyst, the compounds of Chemical Formulae 8 and 9 function as an alkylating agent for the transition metal compound, and the compounds of Chemical Formulae 10 and 11 function as an activating agent for the transition metal compound or the alkylated transition metal compound.

More specifically, the compound of Chemical Formula 8 may be an alkyl aluminoxane, and herein, the alkyl group is as described above. Even more specifically, the compound of Chemical Formula 8 may include methyl aluminoxane, ethyl aluminoxane, isobutyl aluminoxane, butyl aluminoxane or the like, and any one, or a mixture of two or more thereof may be used. Even more specifically, the compound of Chemical Formula 8 may be methyl aluminoxane.

In addition, the compound of Chemical Formula 9 may be more specifically an alkyl aluminum or an alkyl boron, and herein, the alkyl group is as described above. Even more specifically, the compound of Chemical Formula 9 may include trimethyl aluminum, triethyl aluminum, triisobutyl aluminum, tripropyl aluminum, tributyl aluminum, dimethyl chloroaluminum, triisopropyl aluminum, tri-s-butyl aluminum, tricyclopentyl aluminum, tripentyl aluminum, triisopentyl aluminum, trihexyl aluminum, trioctyl aluminum, ethyldimethyl aluminum, methyldiethyl aluminum, triphenyl aluminum, tri-p-tolyl aluminum, dimethyl aluminum methoxide, dimethyl aluminum ethoxide, trimethyl boron, triethyl boron, triisobutyl boron, tripropyl boron, tributyl boron or the like, and any one, or a mixture of two or more thereof may be used. Even more specifically, the compound of Chemical Formula 9 may be trimethyl aluminum, triethyl aluminum or triisobutyl aluminum.

In addition, the compounds of Chemical Formulae 10 and 11 include a non-coordinative bonding anion compatible a cation, a BrØsted acid, and herein, the anion may contain a single coordinate bonding complex compound having a relatively large size and including metalloids. More specifically, the compounds of Chemical Formulae 10 and 11 may be a salt containing an anion including a coordinate bonding complex compound containing a single boron atom in the anion part.

Specific examples of such compounds may include trialkyl ammonium salts such as trimethyl ammonium tetrakis(pentafluorophenyl)borate, triethyl ammonium tetrakis(pentafluorophenyl)borate, tripropyl ammonium tetrakis(pentafluorophenyl)borate, tri(n-butyl)ammonium tetrakis(pentafluorophenyl)borate, tri(2-butyl)ammonium tetrakis(pentafluorophenyl)borate, N,N-dimethyl anilinium tetrakis(pentafluorophenyl)borate, N,N-dimethyl anilinium n-butyltris(pentafluorophenyl)borate, N,N-dimethyl anilinium benzyltris(pentafluorophenyl)borate, N,N-dimethyl anilinium tetrakis(4-(t-butyldimethylsilyl)-2,3,5,6-tetrafluorophenyl)borate, N,N-dimethyl anilinium tetrakis(4-triisopropylsilyl)-2,3,5,6-tetrafluorophenyl)borate, N,N-dimethyl anilinium pentafluorophenoxy tris(pentafluorophenyl)borate, N,N-diethyl anilinium tetrakis(pentafluorophenyl)borate, N,N-dimethyl-2,4,6-trimethyl anilinium tetrakis(pentafluorophenyl)borate, trimethyl ammonium tetrakis(2,3,4,6-tetrafluorophenyl)borate, triethyl ammonium tetrakis(2,3,4,6-tetrafluorophenyl)borate, tripropyl ammonium tetrakis(2,3,4,6-tetrafluorophenyl)borate, tri(n-butyl)ammonium tetrakis(2,3,4,6-tetrafluorophenyl)borate, dimethyl(t-butyl)ammonium tetrakis(2,3,4,6-tetrafluorophenyl)borate, N,N-dimethyl anilinium tetrakis(2,3,4,6-tetrafluorophenyl)borate, N,N-diethylanilinium tetrakis(2,3,4,6-tetrafluorophenyl)borate, N,N-dimethyl-2,4,6-trimethyl anilinium tetrakis(2,3,4,6-tetrafluorophenyl)borate, decyldimethyl ammonium tetrakis(pentafluorophenyl)borate, dodecyldimethyl ammonium tetrakis(pentafluorophenyl)borate, tetradecyldimethyl ammonium tetrakis(pentafluorophenyl)borate, hexadecyldimethyl ammonium tetrakis(pentafluorophenyl)borate, octadecyldimethyl ammonium tetrakis(pentafluorophenyl)borate, eicosyldimethyl ammonium tetrakis(pentafluorophenyl)borate, methyldidecyl ammonium tetrakis(pentafluorophenyl)borate, methyldidodecyl ammonium tetrakis(pentafluorophenyl)borate, methylditetradecyl ammonium tetrakis(pentafluorophenyl)borate, methyldihexadecyl ammonium tetrakis(pentafluorophenyl)borate, methyldioctadecyl ammonium tetrakis(pentafluorophenyl)borate, methyldieicosyl ammonium tetrakis(pentafluorophenyl)borate, tridecyl ammonium tetrakis(pentafluorophenyl)borate, tridodecyl ammonium tetrakis(pentafluorophenyl)borate, tritetradecyl ammonium tetrakis(pentafluorophenyl)borate, trihexadecyl ammonium tetrakis(pentafluorophenyl)borate, trioctadecyl ammonium tetrakis(pentafluorophenyl)borate, trieicosyl ammonium tetrakis(pentafluorophenyl)borate, decyldi(n-butyl)ammonium tetrakis(pentafluorophenyl)borate, dodecyldi(n-butyl)ammonium tetrakis(pentafluorophenyl)borate, octadecyldi(n-butyl)ammonium tetrakis(pentafluorophenyl)borate, N,N-didodecyl anilinium tetrakis(pentafluorophenyl)borate, N-methyl-N-dodecyl anilinium tetrakis(pentafluorophenyl)borate or methyldi(dodecyl)ammonium tetrakis(pentafluorophenyl)borate; dialkyl ammonium salts such as di-(i-propyl)ammonium tetrakis(pentafluorophenyl)borate or dicyclohexyl ammonium tetrakis(pentafluorophenyl)borate; carbonium salts such as tropylium tetrakis(pentafluorophenyl)borate, triphenyl methylium tetrakis(pentafluorophenyl)borate or benzene(diazonium) tetrakis(pentafluorophenyl)borate, or the like, and any one, or a mixture of two or more thereof may be used. Even more specifically, the compounds of Chemical Formulae 10 and 11 may include N,N-dimethyl anilinium tetrakis(pentafluorophenyl)borate, tributyl ammonium tetrakis(pentafluorophenyl)borate, di(octadecyl)methyl ammonium tetrakis(pentafluorophenyl)borate, di(octadecyl)(n-butyl)ammonium tetrakis(pentafluorophenyl)borate, triphenyl methylium tetrakis(pentafluorophenyl)borate, tropylium tetrakis(pentafluorophenyl)borate, or the like.

The transition metal compound of Chemical Formula 1 and the co-catalyst may be used in a form impregnated in a carrier, and herein, an inorganic carrier such as silica or alumina may be used as the carrier. Using in a form impregnated in an inorganic carrier as above may be useful for slurry polymerization or gas-phase polymerization in the polymerization for preparing an olefin-based polymer thereafter.

The catalyst composition having compositions as above may be prepared using common methods, and specifically, may be prepared using a preparation method (first method) including obtaining a mixture by bringing the transition metal compound of Chemical Formula 1 into contact with the alkylating agent of Chemical Formula 8 or 9, and adding the activating agent of Chemical Formula 10 or 11 to the mixture, or may be prepared using a preparation method (second method) including bringing the transition metal compound of Chemical Formula 1 into contact with the activating agent of Chemical Formula 10 or 11.

In the first method, a molar ratio of the alkylating agent of Chemical Formula 8 or 9 with respect to the transition metal compound of Chemical Formula 1 may be 1:2 to 5,000, more specifically, 1:10 to 1,000, and even more specifically 1:20 to 500. In addition, a molar ratio of the activating agent of Chemical Formula 10 or 11 with respect to the transition metal compound of Chemical Formula 1 may be 1:1 to 25, more specifically 1:1 to 10, and even more specifically 1:1 to 5. When a molar ratio of the alkylating agent of Chemical Formula 8 or 9 with respect to the transition metal compound of Chemical Formula 1 is less than 1:2, the amount of the alkylating agent is excessively small, which may lead to concern of transition metal compound alkylation not being sufficiently progressed, and when the molar ratio is greater than 1:5,000, activation of the alkylated transition metal compound may be difficult due to a side reaction between the excess alkylating agent and the activating agent of Chemical Formula 10 or 11 added afterward. In addition, when a molar ratio of the activating agent of Chemical Formula 10 or 11 with respect to the transition metal compound of Chemical Formula 1 is less than 1:1, the amount of the alkylating agent is relatively small causing insufficient activation of the transition metal compound, which may lead to concern of greatly reducing activity of the produced catalyst composition, and the molar ratio being greater than 1:25 may cause concern of cost increases in preparing the catalyst composition due to excessive use of the activating agent, and decline in the purity of the produced polymer.

In the second method, a molar ratio of the activating agent of Chemical Formula 10 or 11 with respect to the transition metal compound of Chemical Formula 1 may be 1:1 to 500, more specifically 1:1 to 50, and even more specifically 1:2 to 25. When the molar ratio is less than 1:1, the amount of the alkylating agent is relatively small causing incomplete activation of the transition metal compound, which may lead to concern of reducing activity of the produced catalyst composition, and the molar ratio being greater than 1:500 may cause concern of cost increases in preparing the catalyst composition due excessive use of the activating agent, and decline in the purity of the produced polymer.

In addition, in the preparation of the catalyst composition, aliphatic hydrocarbon-based solvents such as pentane, hexane or heptane; or aromatic-based solvents such as benzene or toluene may be used as a reaction solvent, however, the solvent is not limited thereto, and all solvents capable of being used in the art may be used.

As described above, the catalyst composition according to one embodiment of the present disclosure includes the transition metal compound of Chemical Formula 1 having excellent structural stability as well as structurally very facilitating monomer approaches, and therefore, may exhibit excellent polymerization reactivity, and particularly, may exhibit excellent reactivity for olefin monomers having large steric hindrance.

In addition, by including the co-catalyst as above together with the transition metal compound, the co-catalyst activates the transition metal compound to a proper degree and suppresses the production of excessively long polymer chains in preparing an olefin-based polymer, and meanwhile, the transition metal compound and the co-catalyst randomize bonding of olefin-based monomers, and as a result, an olefin-based polymer having low crystallization temperature and melting temperature as well as having low density may be prepared.

The catalyst composition is capable of being used in various fields, and among these, may be useful in preparing an olefin-based polymer, particularly, in preparing a low density ethylene polymer or a copolymer of ethylene and alpha-olefin.

Accordingly, another embodiment of the present disclosure provides an olefin-based polymer prepared using the catalyst composition.

The olefin-based polymer may be prepared according to common methods for preparing an olefin-based polymer except that the catalyst composition is used. Specifically, the olefin-based polymer brings the catalyst composition into contact with one or more olefin monomers for polymerization reaction, and as a result, may be prepared to an olefin-based homopolymer or copolymer. Specifically, the olefin-based polymer may be an ethylene homopolymer, or a copolymer of ethylene and α-olefin.

The polymerization for preparing the olefin-based polymer may be carried out using various methods such as slurry polymerization, liquid-phase polymerization, gas-phase polymerization or bulk polymerization, and more specifically, may be carried out through liquid-phase polymerization.

When the polymerization is carried out through liquid-phase polymerization, olefin monomers may be dissolved and diluted in a solvent for polymerization such as an aliphatic hydrocarbon solvent having 5 to 12 carbon atoms (for example, pentane, hexane, heptane, nonane, decane, isomers thereof or the like); an aromatic hydrocarbon solvent having 6 to 20 carbon atoms (for example, toluene, benzene or the like) or a chlorinated hydrocarbon-based solvent (for example, dichloromethane, chlorobenzene or the like) to be used. Herein, small amounts of water, air or the like functioning as a catalyst poison and reducing catalytic activity for the solvent for polymerization may be removed using an alkyl aluminum.

In addition, specific examples of the monomer for preparing the olefin-based polymer may include ethylene, alpha-olefin, cyclic olefin or the like, and in addition thereto, diene olefin-based monomers or triene olefin-based monomers having two or more double bonds, and the like, may also be used. More specifically, examples of the olefin-based monomer may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, l-eicosene, norbornene, norbornadiene, ethylidene norbornene, phenyl norbornene, vinyl norbornene, dicyclopentadiene, 1,4-butadiene, 1,5-pentadiene, 1,6-hexadiene, styrene, alpha-methylstyrene, divinylbenzene or 3-chloromethylstyrene, 2,3-diisoprophenylidene-5-norbornenene, 2-ethylidene-3-isopropylidene-5-norbornene, 2-prophenyl-2,5-norbornadiene, 1,3,7-octatriene, 1,4,9-decatriene or the like, and any one, or a mixture of two or more thereof may be used.

In addition, when preparing a copolymer of ethylene and α-olefin as the olefin-based polymer, α-olefin having 3 to 18 carbon atoms may be used as a co-monomer together with ethylene. Specifically, examples of the α-olefin may include propylene, 1-butene, 1-pentene, 4-methyl-1-pentene, 1-hexene, 1-octene, 1-decene, 1-dodecene, 1-hexadecene, 1-octadecene or the like, and any one, or a mixture of two or more thereof may be used. More specifically, 1-butene, 1-hexene, 1-octene or 1-decene may be used.

When preparing the copolymer, the α-olefin may be used in the content to make the ethylene content in the finally prepared copolymer 50% by weight or greater, more specifically 60% by weight or greater and even more specifically from 60% by weight to 99% by weight.

In addition, a process for preparing the olefin polymer may be carried out at 20° C. to 500° C., more specifically at 25° C. to 200° C. and even more specifically at 50° C. to 100° C. Herein, the reaction pressure may be from 0.1 bar to 7 bar and more specifically from 1 bar to 5 bar.

The polymer prepared using the preparation method as above has high molecular weight and low density by using the catalyst composition including the transition metal compound of Chemical Formula 1.

Specifically, the polymer has low density of 0.9 g/cc or less, more specifically 0.885 g/cc or less and even more specifically 0.85 g/cc to 0.885 g/cc, and at the same time, may have a melt index (MI) of 1 g/min to 20 g/min and more specifically 3 g/min to 18 g/min under a load of 2.16 kg. By having such low density and high molecular weight properties, excellent mechanical properties such as rigidity and impact resistance may be obtained. In the present disclosure, the melt index may be measured in accordance with the ASTM D-1238 (condition E, 190° C., 2.16 Kg load).

In addition to the low density and high molecular weight properties, the polymer may have a crystallization temperature (Tc) of 80° C. or lower, more specifically 75° C. or lower and even more specifically 60° C. to 75° C.; and a melting temperature of 100° C. or lower, more specifically 90° C. or lower and even more specifically 80° C. to 85° C. By having lower crystallization temperature and melting temperature compared to existing olefin-based polymers, more superior processability may be obtained.

In the present disclosure, Tc and Tm may be measured using a differential scanning calorimeter (DSC) 2920 manufactured by TA Corporation, and herein, the measured values are obtained through second melt raising the temperature by 10° C. per minute in order to remove thermal history of the polymer. In the measured DSC curve, Tc is a maximum point of the exothermic peak in the cooling, and Tm is a maximum point of the endothermic peak in the second temperature raising.

The olefin-based polymer having physical properties as above may be used in various fields and applications such as for automobiles, for wires, for toys, for fibers, for medicines, for constructions or for consumer goods.

Another embodiment of the present disclosure provides the ligand compound of Chemical Formula 2 useful in preparing the transition metal compound of Chemical Formula 1.

The ligand compound of Chemical Formula 2 is the same as described above.

Specifically, the ligand compound of Chemical Formula 2 may be a compound selected from the group consisting of the following Chemical Formulae 2-1 to 2-4.

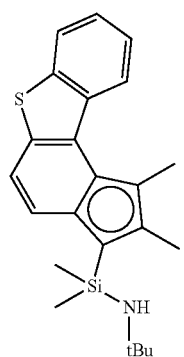

(2-1)

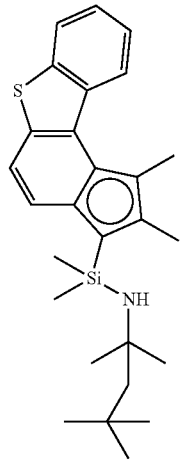

(2-2)

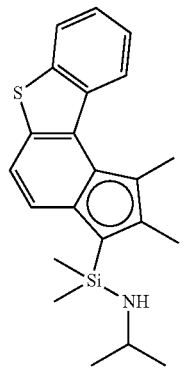

(2-3)

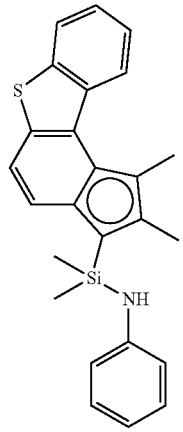

(2-4)

The ligand compound of Chemical Formula 2 according to one embodiment of the present disclosure includes a linking structure of a dibenzothiophene-fused cyclopentadienyl group and a silyl group introducing an amino group into the molecule, and therefore, is capable of enhancing structural stability of the transition metal compound by forming a rigid pentagonal ring when forming coordinate bonds with the metal, and is capable of enhancing thermal stability of a catalyst due to high electron density around the transition metal, and in addition thereto, is capable of preparing a high molecular weight and yet low density copolymer since monomer approaches are readily achieved structurally in the copolymerization of ethylene and monomers having large steric hindrance.

The ligand compound of Chemical Formula 2 is an intermediate obtained when preparing the transition metal compound of Chemical Formula 1, but may also be used in other applications.

Hereinafter, examples of the present disclosure will be described in detail so that those skilled in the art may readily carry out the present disclosure. However, the present disclosure may be implemented in many different forms, and is not limited to the examples described herein.

Synthesis of Ligand and Transition Metal Compound

Organic reagents and solvents were purchased from Aldrich and purified using a standard method to be used unless particularly mentioned otherwise. Contact with air and moisture was blocked in all synthesis steps in order to enhance the reproducibility of experiments. CGC [Me$_2$Si(Me$_4$C$_5$)NtBu]TiMe$_2$ (Constrained-Geometry Catalyst, abbreviated as CGC hereinafter) of Comparative Example 1 was synthesized according to U.S. Pat. No. 6,015,916.

Preparation Example 1-1: Preparation of Ligand 10 g of dibenzothiophene was dissolved in 50 ml of methylene chloride (MC) in a Schlenk flask. 9.8 g of AlCl$_3$, 60 ml of MC, and tigloyl chloride were stirred in another Schlenk flask, and the dibenzothiophene solution dissolved in MC previously was slowly added thereto at −78° C., and reacted. After reacting overnight, the reaction solution was transferred to 0° C. ice water via a cannula, and then the resulting reactant was extracted with MC and a supersaturated K$_2$CO$_3$ solution to obtain a ketone-based compound (i) of the following structure.

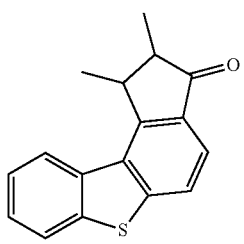

(i)

After dissolving 11.2 g (42.05 mmol) of the obtained ketone-based compound (i) in 80 ml of methanol and 80 ml of tetrahydrofuran, 1 eq. of NaBH$_4$ was added in a powder state thereto at 0° C., and reacted. After progressing the reaction overnight, water was added thereto for quenching. The resultant reactant was extracted with ether to separate the organic layer, and 12 N HCl was added thereto to obtain 1,2-dimethyl-1H-benzo[b]indeno[4,5-d]thiophene (ii) of the following structure.

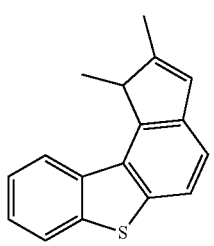

(ii)

1 g (3.994 mmol) of the 1,2-dimethyl-1H-benzo[b]indeno[4,5-d]thiophene (ii) prepared above was weighed and added to a 100 ml Schlenk flask, and then 20 ml of tetrahydrofuran (THF) was introduced thereto. 1.1 eq. of 2.5 M in n-BuLi hexane solution reagent was dropped thereto at −78° C. During the dropwise addition, the color of the reaction solution changed from a reddish brown color to a wine color. After stirring the result for 1 hour at −78° C., the temperature of the reaction solution was raised to room temperature (20±5° C.), and the reaction solution was stirred overnight. In a separate Schlenk flask, 1.46 ml of dichlorodimethylsilane was dissolved in 14.6 ml of THF, and then the reaction solution prepared above was added thereto at −78° C., and reacted. After the reaction was complete, the result was vacuum dried, stirred and mixed after adding hexane, and then celite filtered to obtain a yellow product (iii) of the following structure.

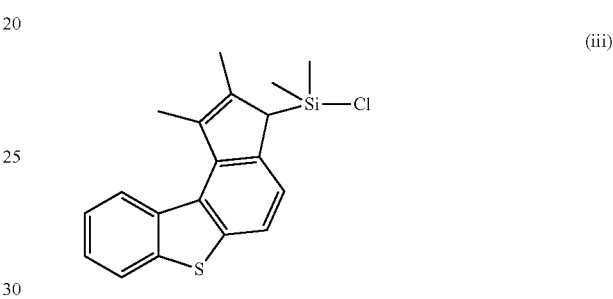

(iii)

To 220 mg (0.64 mmol) of the obtained product (iii), 3 ml of hexane was introduced to prepare a solution. After introducing t-BuNH$_2$ (2 eq., 0.14 ml) and 3 ml of hexane into a separate Schlenk flask, n-BuLi was added dropwise thereto at −78° C. After stirring the result for 10 minutes at −78° C., the temperature was raised and the result was stirred for 5 hours at room temperature (20±5° C.), and then the solution prepared above was added thereto at −78° C., and reacted. After reacting overnight, the result was vacuum dried, stirred after introducing hexane thereto, dissolved in hexane, and then celite filtered to obtain a ligand compound (2-1) of N-tert-butyl-1-(1,2-dimethyl-3H-benzo[b]indeno[4,5-d]thiophen-3-yl)-1,1-dimethylsilanamine.

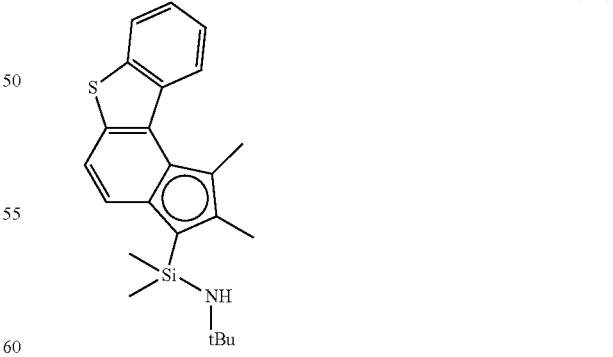

(2-1)

Preparation Example 1-2: Preparation of Ligand Compound

A ligand compound (2-2) of 1-(1,2-dimethyl-3H-benzo[b]indeno[4,5-d]thiophen-3-yl)-1,1-dimethyl-N-(2,4,4-trimethylpentan-2-yl)silanamine of the following structure was prepared in the same manner as in Preparation Example 1-1, except that 2,4,4-trimethylpentane-2-amine was used instead of t-BuNH$_2$.

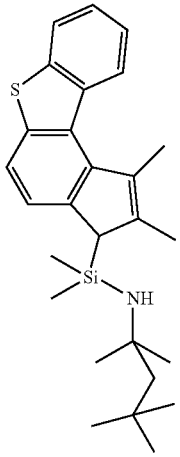

(2-2)

Preparation Example 1-3: Synthesis of Ligand Compound 1-(1,2-dimethyl-3H-benzo[b]indeno[4,5-d]thiophen-3-yl)-N-isopropyl-1,1-dimethylsilanamine (2-3) of the following structure was prepared in the same manner as in Preparation Example 1-1, except that isopropylamine was used instead of t-BuNH$_2$.

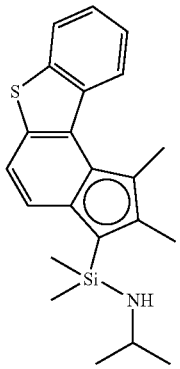

(2-3)

Preparation Example 1-4: Preparation of Ligand 1-(1,2-dimethyl-3H-benzo[b]indeno[4,5-d]thiophen-3-yl)-1,1-dimethyl-N-phenylsilanamine (2-4) of the following structure was prepared in the same manner as in Preparation Example 1-1, except that phenylamine was used instead of t-BuNH$_2$.

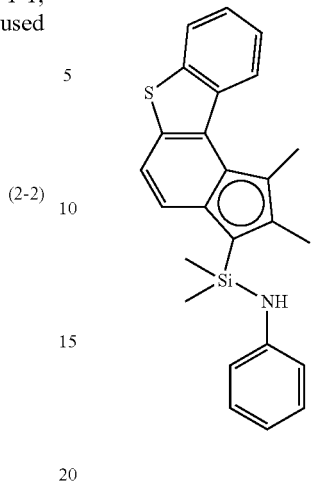

(2-4)

Preparation Example 2-1: Synthesis of Transition Metal Compound

To a 20 ml Schlenk flask, the ligand compound (2-1) of N-tert-butyl-1-(1,2-dimethyl-3H-benzo[b]indeno[4,5-d]thiophen-3-yl)-1,1-dimethylsilanamine prepared in Preparation Example 1-1 (100.8 mg, 0.2655 mmol) and 2.6 ml of toluene were introduced, and stirred first. n-BuLi (0.22 ml, 2.05 eq., concentration in hexane: 2.5 M) was added thereto at −30° C., and the result was reacted overnight at room temperature (20±5° C.). After that, MeMgBr (0.21 ml, 2.4 eq., concentration in diethyl ether: 3.0 M) was slowly added dropwise thereto at −30° C., then TiCl$_4$ (0.26 ml, 1.0 eq., concentration in toluene: 1.0 M) was added thereto in order, and the result was reacted overnight at room temperature (20±5° C.). After that, the reaction mixture passed through a celite using hexane to be filtered. The solvent was dried to obtain a transition metal compound (1-1) in a brown solid form having the following chemical structure.

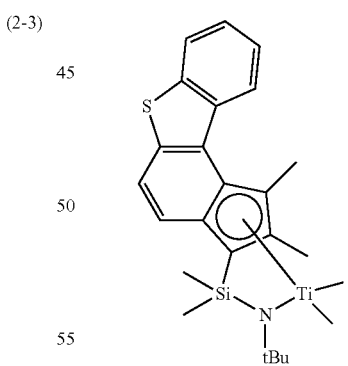

(1-1)

$^1$H-NMR (in C$_6$D$_6$, 500 MHz): 8.81 (d, 1H), 7.62 (d, 1H), 7.58 (d, 1H), 7.29 (m, 2H), 7.12 (1H), 2.82 (s, 3H), 1.95 (s, 3H), 1.46 (s, 9H), 0.79 (3H), 0.65 (3H), 0.59 (3H), −0.26 (3H)

Preparation Example 2-2: Synthesis of Transition Metal Compound

A transition metal compound (1-2) was prepared in the same manner as in Preparation Example 2-1, except that the ligand compound (2-2) prepared in Preparation Example 1-2 was used instead of the ligand compound (2-1) prepared in Preparation Example 1-1.

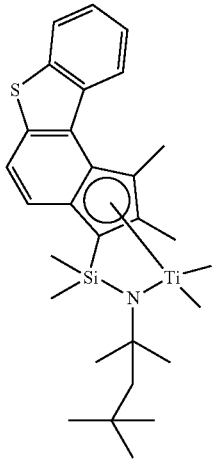

(1-2)

$^1$H-NMR (in C$_6$D$_6$, 500 MHz): 8.8 (d, 1H), 7.62 (d, 1H), 7.58 (d, 1H), 7.25 (3H), 2.82 (s, 3H), 1.97 (s, 3H), 1.94 (s, 2H), 1.64 (s, 3H), 1.58 (s, 3H), 0.99 (s, 9H), 0.79 (s, 3H), 0.65 (s, 3H), 0.59 (s, 3H), −0.26 (s, 3H)

Preparation Example 2-3: Synthesis of Transition Metal Compound

A transition metal compound (1-3) was prepared in the same manner as in Preparation Example 2-1, except that the ligand compound (2-3) prepared in Preparation Example 1-3 was used instead of the ligand compound (2-1) prepared in Preparation Example 1-1.

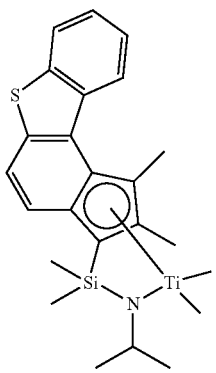

(1-3)

$^1$H-NMR (in C$_6$D$_6$, 500 MHz): 8.86 (d, 1H), 7.63 (d, 1H), 7.52 (d, 1H), 7.28 (m, 3H), 4.94 (q, 1H), 2.83 (s, 3H), 1.96 (s, 3H), 2.21 (d, 3H), 2.21 (d, 3H), 0.67 (s, 3H), 0.54 (s, 3H), 0.49 (s, 3H), −0.35 (s, 3H)

Preparation Example 2-4: Synthesis of Transition Metal Compound

A transition metal compound (1-4) was prepared in the same manner as in Preparation Example 2-1, except that the ligand compound (2-4) prepared in Preparation Example 1-4 was used instead of the ligand compound (2-1) prepared in Preparation Example 1-1.

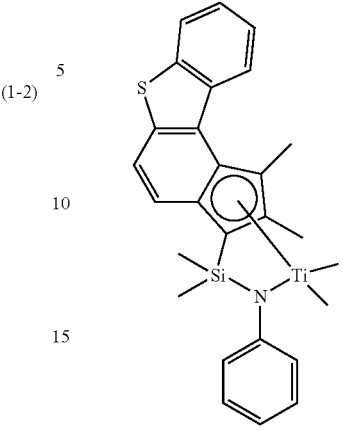

(1-4)

$^1$H-NMR (in CDCl$_3$, 500 MHz): 8.78 (d, 1H), 8.17 (m, 1H), 7.95 (d, 1H), 7.87 (m, 1H), 7.66 (1H), 7.57 (t, 3H), 7.51 (t, 3H), 7.08 (d, 3H), 6.96 (t, 1H), 3.09 (s, 3H), 2.36 (s, 3H), 2.28 (s, 3H), 0.80 (s, 3H), 0.73 (s, 3H), −0.44 (s, 3H)

Example 1: Preparation of Ethylene and 1-Octene Copolymer

To a 2 L autoclave reactor, a hexane (1.0 L) solvent and 210 ml of 1-octene were added, and the temperature of the reactor was raised to 150° C. At the same time, inside the reactor was saturated with approximately 35 bar of ethylene. A catalyst-injection cylinder was filled with 2 μmol of the transition metal compound (1-1) of Preparation Example 2-1 treated with triisobutyl aluminum (1.0 M), and a dimethyl anilinium tetrakis(pentafluorophenyl)borate (AB) co-catalyst (10 equivalents), and the result was injected into the reactor. Herein, the copolymerization reaction was progressed for 8 minutes while constantly injecting ethylene so as to maintain the pressure inside the reactor at approximately 35 bar. After completing the polymerization reaction, the remaining ethylene gas was exhausted, and the polymer solution was added to an excess amount of ethanol to induce precipitation. The obtained polymer was washed 3 times each with ethanol and acetone, and dried for 12 hours or longer in a 80° C. vacuum oven.

Examples 2 to 4: Preparation of Ethylene and 1-Octene Copolymer

Copolymerization was carried out in the same manner as in Example 1 except that each of the transition metal compounds prepared in Preparation Examples 2-2 to 2-4 was used instead of the transition metal compound prepared in Preparation Example 2-1.

Comparative Example: Preparation of Ethylene and 1-Octene Copolymer

Copolymerization was carried out in the same manner as in Example 1 except that a transition metal compound (iv) of the following structure was used instead of the transition metal compound prepared in Preparation Example 2-1. Herein, the following transition metal compound was prepared using a method described in U.S. Pat. No. 976,131.

(iv)

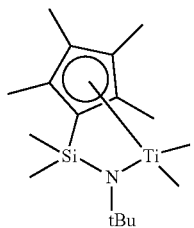

Test Example 1: Physical Property Evaluation

Catalytic activity in preparing the ethylene and 1-octene copolymers according to Examples 1 to 3 and Comparative Example, and a melt index (MI), density, a crystallization temperature (Tc) and a melting temperature (Tm) of the prepared copolymers were each measured using methods as follows, and the results are shown in the following Table 1.

(1) Catalytic activity: obtained from an introduced molar ratio of the transition metal compound with respect to the total amount of the obtained copolymer prepared. In detail, a ratio of the value obtained from measuring a mass of some of the reaction solution taken after the completion of the polymerization reaction, and the value obtained from measuring a mass of the copolymer remaining after removing all the hexane solvent and residual monomers by heating some of the copolymer for 10 minutes at 120° C. was calculated, and, based thereon, catalytic activity was calculated using the mass of the copolymer produced, the molar number of the transition metal compound used in the polymerization reaction, and the polymerization time.

(2) Melt index (MI): measured in accordance with the ASTM D-1238 (condition E, 190° C., 2.16 Kg load).

(3) Density: the sample treated with an antioxidant (1,000 ppm) was prepared to a sheet having a thickness of 3 mm and a radius of 2 cm using a 180° C. press mold, cooled by 10° C./min, and measured in a Mettler balance.

(4) Crystallization temperature (Tc) and melting temperature (Tm): measured using a differential scanning calorimeter (DSC) 2920 manufactured by TA Corporation. In detail, using DSC, the temperature of the copolymer was raised to 200° C. under nitrogen atmosphere, maintained for 5 minutes, and then lowered to 30° C., and then raised again to observe a DSC curve. Herein, the heating rate and the cooling rate were each 10° C./min. In the measured DSC curve, the crystallization temperature was a maximum point of the exothermic peak in the cooling, and the melting temperature was a maximum point of the endothermic peak in the second temperature raising.

TABLE 1

| | Catalytic Activity (kg/mmol(Ti)) | MI (g/10 min) | Density (g/cc) | Tc (° C.) | Tm (° C.) |
|---|---|---|---|---|---|
| Comparative Example | 20 | 25 | 0.904 | 64 | 102 |
| Example 1 | 24 | 18 | 0.884 | 65 | 82 |
| Example 2 | 6 | 3 | 0.885 | 73 | 85 |
| Example 3 | 6 | 4 | 0.871 | 63 | 82 |

As shown in Table 1, some of the catalyst compositions including the transition metal compound according to the present disclosure exhibited lower catalytic activity compared to the existing catalyst composition of Comparative Example, however, regardless of catalytic activity, the 1-octene and ethylene copolymers of Examples 1 to 3 prepared using the catalyst composition including the transition metal compound according to the present disclosure exhibited lower density, MI, Tc and Tm compared to the copolymer of Comparative Example. From such results, it can be seen that the transition metal compounds according to the present disclosure very stably maintain the metal site surroundings in a rigid pentagonal ring structure by the amino group linked to the silyl group bridge in a ring form, and thereby structurally facilitate monomer approaches, and accordingly, have relatively excellent reactivity for olefin monomers having large steric hindrance such as 1-octene, and are capable of preparing very low density and high molecular weight olefin-based polymers having an MI of 20 or less without increasing while having density of 0.9 g/cc or less together with low Tc and Tm.

What is claimed is:
1. A transition metal compound of the following Chemical Formula 1:

[Chemical Formula 1]

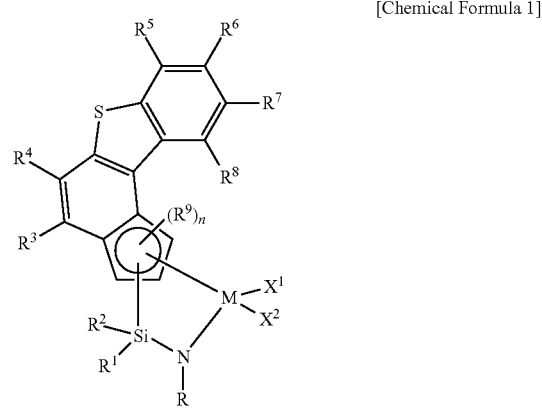

wherein,

M is a group 4 transition metal;

R is selected from the group consisting of an alkyl group having 1 to 20 carbon atoms, a cycloalkyl group having 3 to 20 carbon atoms, an aryl group having 6 to 20 carbon atoms, an arylalkyl group having 7 to 20 carbon atoms, and an alkylaryl group having 7 to 20 carbon atoms;

$R^1$ and $R^2$ are each independently selected from the group consisting of a hydrogen atom, an alkyl group having 1 to 20 carbon atoms, an alkenyl group having 2 to 20 carbon atoms, a haloalkyl group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, and combinations thereof, or $R^1$ and $R^2$ are linked to each other to form an aliphatic ring having 3 to 20 carbon atoms or an aromatic ring having 6 to 20 carbon atoms;

$R^3$ to $R^8$ are each independently selected from the group consisting of a hydrogen atom, a halogen group, an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, an alkoxy group having 1 to 20 carbon atoms, an aryloxy group having 6 to 20 carbon atoms, a silyl group, and combinations thereof, or adjacent two or more functional groups among $R^3$ to $R^8$ are linked to each other to form an aliphatic ring having 3 to 20 carbon atoms or an aromatic ring having 6 to 20 carbon atoms;

$R^9$ is selected from the group consisting of an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, a silyl group, and a metalloid radical of a group 14 metal substituted with a hydrocarbyl group having 1 to 20 carbon atoms;

$X^1$ and $X^2$ are each independently selected from the group consisting of a halogen group, an alkyl group having 1 to 20 carbon atoms, an alkenyl group having 2 to 20 carbon atoms, an aryl group having 6 to 20 carbon atoms, an alkylaryl group having 7 to 20 carbon atoms, an arylalkyl group having 7 to 20 carbon atoms, an alkylamino group having 1 to 20 carbon atoms, an arylamino group having 6 to 20 carbon atoms, and an alkylidene group having 1 to 20 carbon atoms;

R, $R^1$ to $R^9$, $X^1$ and $X^2$ are each independently unsubstituted or substituted with one or more substituents selected from the group consisting of a halogen group, an alkyl group having 1 to 20 carbon atoms, a haloalkyl group having 1 to 20 carbon atoms, an alkenyl group having 2 to 20 carbon atoms, an alkoxy group having 1 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, and an aryloxy group having 6 to 20 carbon atoms; and n is an integer of 1 or 2, and when n is an integer of 2, two $R^9$s are the same as or different from each other.

2. The transition metal compound of claim 1, wherein R is a linear or branched alkyl group having 1 to 8 carbon atoms or an aryl group having 6 to 12 carbon atoms unsubstituted or substituted with one or more substituents selected from the group consisting of a halogen group, an alkyl group having 1 to 10 carbon atoms, and a haloalkyl group having 1 to 10 carbon atoms.

3. The transition metal compound of claim 1, which is selected from the group consisting of the following Chemical Formulae 1a and 1b:

[Chemical Formula 1a]

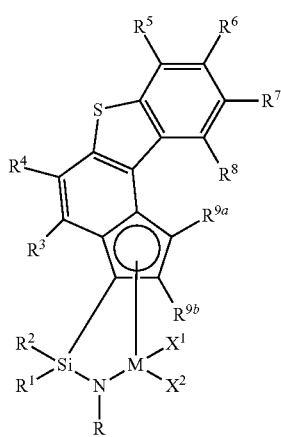

[Chemical Formula 1b]

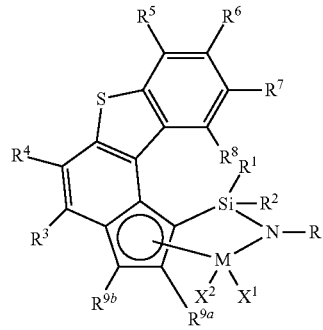

wherein, $R^{9a}$ and $R^{9b}$ are each independently selected from the group consisting of a hydrogen atom, an alkyl group having 1 to 20 carbon atoms, an alkenyl group having 2 to 20 carbon atoms, a cycloalkyl group having 3 to 20 carbon atoms, an aryl group having 6 to 20 carbon atoms, an arylalkyl group having 7 to 20 carbon atoms, an alkylaryl group having 7 to 20 carbon atoms, a silyl group, and a metalloid radical of a group 14 metal substituted with a hydrocarbyl group having 1 to 20 carbon atoms, or $R^{9a}$ and $R^{9b}$ are linked to each other to form an aliphatic ring having 3 to 20 carbon atoms or an aromatic ring having 6 to 20 carbon atoms; and M, R, $R^1$ to $R^8$, $X^1$, and $X^2$ have the same definitions as in claim 1.

4. The transition metal compound of claim 3, wherein M is selected from the group consisting of titanium (Ti), zirconium (Zr), and hafnium (Hf);

R is a linear or branched alkyl group having 1 to 8 carbon atoms or an aryl group having 6 to 12 carbon atoms unsubstituted or substituted with one or more substituents selected from the group consisting of a halogen group, an alkyl group having 1 to 10 carbon atoms, and a haloalkyl group having 1 to 10 carbon atoms;

$R^1$ and $R^2$ are each independently selected from the group consisting of an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms, and an alkylaryl group having 7 to 12 carbon atoms, or $R^1$ and $R^2$ are linked to each other to form an aliphatic ring having 4 to 6 carbon atoms or an aromatic ring having 6 to 8 carbon atoms;

$R^3$ to $R^8$ are each independently selected from the group consisting of a hydrogen atom, an alkyl group having 1 to 6 carbon atoms, an alkenyl group having 2 to 6 carbon atoms, a cycloalkyl group having 3 to 6 carbon atoms, an aryl group having 6 to 12 carbon atoms, an arylalkyl group having 7 to 12 carbon atoms, and an alkylaryl group having 7 to 12 carbon atoms, or adjacent two or more functional groups among $R^3$ to $R^8$ are linked to each other to form an aliphatic ring having 4 to 6 carbon atoms or an aromatic ring having 6 to 8 carbon atoms; and $R^{9a}$ and $R^{9b}$ are each independently selected from the group consisting of a hydrogen atom, an alkyl group having 1 to 8 carbon atoms, a cycloalkyl group having 3 to 12 carbon atoms, an aryl group having 6 to 12 carbon atoms, an arylalkyl group having 7 to 12 carbon atoms, and an alkylaryl group having 7 to 12 carbon atoms, or $R^{9a}$ and $R^{9b}$ are linked to each other to form an aliphatic ring having 4 to 6 carbon atoms or an aromatic ring having 6 to 8 carbon atoms.

5. The transition metal compound of claim 1, which is selected from the group consisting of compounds of the following Chemical Formulae 1-1 to 1-4:

(1-1)

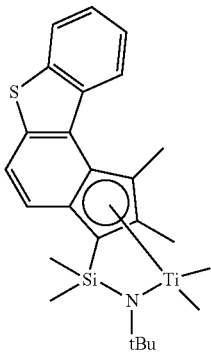

(1-2)

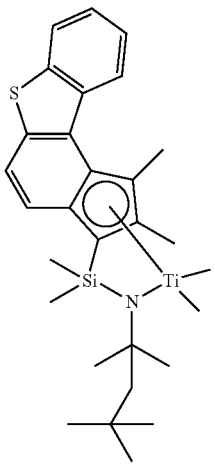

(1-3)

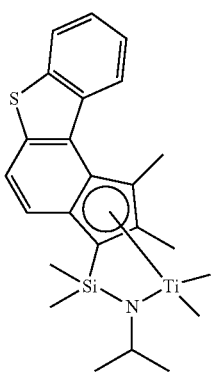

(1-4)

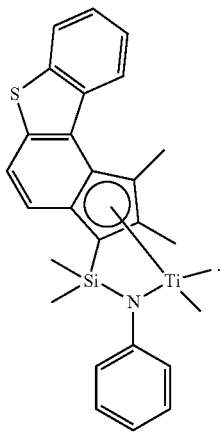

6. A catalyst composition comprising the transition metal compound of claim 1.

7. The catalyst composition of claim 6, further comprising any one, or two or more co-catalysts selected from the group consisting of compounds of the following Chemical Formulae 8 to 11:

—[Al($R^{31}$)—O]$_a$—      [Chemical Formula 8]

A($R^{32}$)$_3$      [Chemical Formula 9]

[L-H]$^+$[W(D)$_4$]$^-$      [Chemical Formula 10]

[L]$^+$[W(D)$_4$]$^-$      [Chemical Formula 11]

wherein, $R^{31}$ and $R^{32}$ are each independently selected from the group consisting of a halogen group, a hydrocarbyl group having 1 to 20 carbon atoms, and a hydrocarbyl group having 1 to 20 carbon atoms substituted with a halogen group;

A is aluminum or boron;

D's are each independently an aryl group having 6 to 20 carbon atoms or an alkyl group having 1 to 20 carbon atoms in which one or more hydrogen atoms are optionally substituted with a substituent, and herein, the substituent is at least any one selected from the group consisting of a halogen group, a hydrocarbyl group having 1 to 20 carbon atoms, an alkoxy group having 1 to 20 carbon atoms, and an aryloxy group having 6 to 20 carbon atoms;

H is a hydrogen atom;

L is a neutral or cationic Lewis acid;

W is a group 13 element; and a is an integer of 2 or greater.

\* \* \* \* \*